United States Patent [19]

Vantard

[11] Patent Number: 4,767,526

[45] Date of Patent: Aug. 30, 1988

[54] ARTIFICIAL KIDNEY WITH AUTOMATIC REGULATION OF THE PRESSURE OF THE DIALYSLATE AS A FUNCTION OF WITHDRAWAL OF ULTRAFILTRATE

[75] Inventor: Georges Vantard, Gournay sur Marne, France

[73] Assignee: Hospal Industrie, Meyzieu, France

[21] Appl. No.: 703,697

[22] Filed: Feb. 21, 1985

Related U.S. Application Data

[63] Continuation of Ser. No. 488,134, Apr. 25, 1983, abandoned, which is a continuation of Ser. No. 278,598, Jun. 29, 1981, abandoned.

[30] Foreign Application Priority Data

Aug. 1, 1980 [FR] France ............................. 80 17326

[51] Int. Cl.⁴ ............................................ B01D 13/00
[52] U.S. Cl. .................... 210/128; 210/257.2; 210/321.65; 210/327.71; 210/321.72; 210/929
[58] Field of Search ............... 210/111, 126, 128, 129, 210/136, 137, 195.2, 257.2, 321.1–321.5, 929, 321.65, 321.71, 321.72

[56] References Cited

U.S. PATENT DOCUMENTS

| | | | |
|---|---|---|---|
| 3,946,731 | 3/1976 | Lichtenstein | 210/87 X |
| 4,021,341 | 5/1977 | Cosentino et al. | 210/87 |
| 4,024,059 | 5/1977 | Sausse | 210/195.2 |
| 4,191,646 | 3/1980 | Larsson et al. | 210/137 X |
| 4,267,041 | 5/1981 | Schael | 210/257.2 X |
| 4,298,357 | 11/1981 | Pernic | 210/137 X |
| 4,348,280 | 9/1982 | George et al. | 210/136 |

Primary Examiner—Richard V. Fisher
Assistant Examiner—W. Gary Jones
Attorney, Agent, or Firm—Gerald D. Sharkin; Robert S. Honor; Walter F. Jewell

[57] ABSTRACT

Artificial kidney comprises a hemodialyzer connected in a dialysis liquid circuit which is in the form of a loop the volume of which is essentially invariable. The circuit is open to the atmosphere and comprises a circulating pump arranged upstream of the hemodialyzer. Means are provided for drawing off and measuring, outside the said circuit, amounts of liquid equal to the amounts of ultrafiltrate which it is desired to remove from a patient's blood stream. A variable hydraulic resistance is provided downstream of the hemodialyzer and comprises a float, the resistance being operative to keep the dialysis liquid at an essentially constant level in the circuit in order automatically to regulate the pressure of the dialysis liquid in the hemodialyzer.

6 Claims, 2 Drawing Sheets

ARTIFICIAL KIDNEY WITH AUTOMATIC REGULATION OF THE PRESSURE OF THE DIALYSLATE AS A FUNCTION OF WITHDRAWAL OF ULTRAFILTRATE

This is a continuation of application Ser. No. 488,134 filed Apr. 25, 1983, now abandoned; which application is a continuation of application Ser. No. 287,598 filed June 29, 1981 now abandoned.

The present invention relates to an artificial kidney and a process using such kidney to purify blood. It relates more particularly to a device for automatic regulation of the pressure of the dialysis liquid as a function of the amounts of ultrafiltrate which it is desired to withdraw from the blood of a patient, according to the particular treatment envisaged for each hemodialysis session.

Artificial kidneys have already been proposed which possess means for imposing the envisaged amount of ultrafiltrate which must be withdrawn from a patient during each treatment.

However, the use of these artificial kidneys can require fairly significant means in terms of equipment or qualified personnel.

An object of the present invention is the provision of an artificial kidney of simple, economical and safe construction, the operation of which is reliable and partially automatic and permits a precise control over the ultrafiltrate withdrawn from a patient.

Further objects of the present invention will become apparent during the description which now follows.

According to one aspect of the invention there is provided in an artificial kidney comprising a circuit for the dialysis liquid including a hemodialyzer and a circulating pump upstream of the said hemodialyzer, the said circuit being formed as a loop of constant volume, being open to the atmosphere and being provided with means for drawing off a volume of dialysis liquid from the circuit and means for measuring the volume of dialysis liquid drawn off, the provision in the circuit downstream of the hemodialyzer of a variable hydraulic resistance including means responsive to the maintenance of an essentially constant level of liquid in the loop circuit to regulate automatically the pressure of the dialysis liquid in the hemodialyzer.

A further aspect of this invention provides in a process for purifying the blood by dialysis and ultrafiltration, wherein a dialysis liquid is circulated in a loop circuit which is of essentially constant volume, which is open to the atmosphere and which includes a hemodialyzer, the steps of regulating the average pressure of the dialysis liquid in the hemodialyzer automatically to values between atmospheric pressure and the average pressure of the blood in the hemodialyzer, in order to maintain an essentially constant level of the liquid in the said loop circuit, and drawing off from the circuit an amount of liquid equal to the amount of ultrafiltrate which it is desired to draw off, the amount of liquid drawn off being measured outside the said circuit.

BRIEF DESCRIPTION OF THE DRAWINGS

In order to make the invention easier to understand, the homologous elements in the various figures carry the same numbers.

With reference to FIG. 1, the artificial kidney illustrated therein possesses a hemodialyzer (10) divided into two compartments (12) and (13) by a membrane (11) which simultaneously permits the dialysis and the ultrafiltration of the blood. The blood to be treated, which is delivered by a circulating pump (14), passes through the compartment (12). The dialysis liquid passes through the compartment (13), preferably in countercurrent to the blood, as indicated by the arrows.

Figure 1:
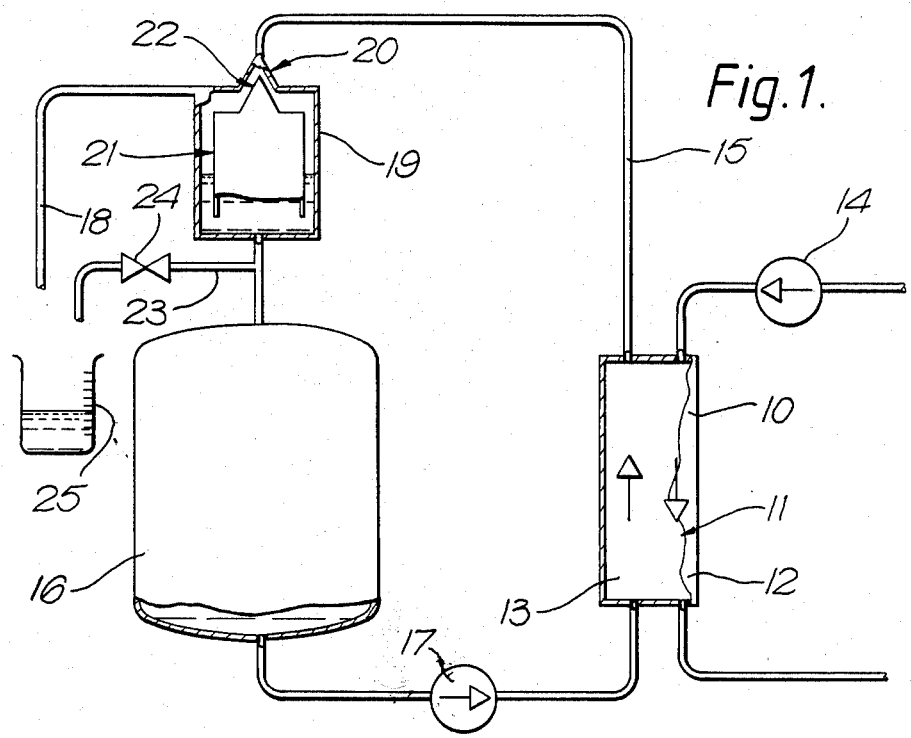
FIG. 1 is the diagram of a first preferred embodiment of an artificial kidney according to the invention.

The dialysis liquid circuit (15) forms a loop in itself; it possesses a reservoir (16), the volume of which is not critical, and also conventional heating means (not shown) for the dialysis liquid. The dialysis liquid moves under the action of a circulating pump (17) located upstream of the hemodialyzer and preferably connected directly to the orifice where the dialysis liquid enters the hemodialyzer. This loop circuit, which consists of the reservoir (16) and the elements connecting it to the hemodialyzer (10), is essentially invariable, that is to say that it preserves a virtually constant internal volume, regardless of the stresses to which it can normally be subjected. As this circuit is open to the atmosphere, by virtue of a tube (18), these stresses are generally small and its construction is hence economical.

This circuit comprises a variable hydraulic resistance located downstream of the hemodialyzer, that is to say preferably connected directly to the orifice where the dialysis liquid leaves the hemodialyzer. The term "variable hydraulic resistance" is understood as meaning any suitable mechanical means which makes it possible to adjust the pressure of a fluid to a desired value by means of a local pressure loss. In FIG. 1, this variable hydraulic resistance consists of an obturator, the moving part of which is integral with a float. For this purpose, a chamber (19) is provided in its upper part with an orifice (20) for the introduction of the dialysis liquid. This orifice, which has a vertical axis, is preferably downwardly flared, the walls defining the orifice forming a vertical cone.

A float (21), surmounted by a preferably conical point (22), cooperates with the flared orifice (20) so as to form a blocking device capable of ensuring a function of automatic regulation of the pressure of the dialysis liquid. Pushed upwardly by the float, the point (22) can totally block the orifice (20). As soon as the float starts to descend, the point disengages and partially frees the orifice (20). The variable hydraulic resistance is thus controlled by the maintenance of an essentially constant level of dialysis liquid in the chamber (19), and the pressure of the dialysis liquid upstream, in particular in the hemodialyzer, is thus regulated automatically.

The variable hydraulic resistance receives, from the dialysis liquid, both the information for its control and the driving energy for its operation. Thus, the pressure of the dialysis liquid in the hemodialyzer is regulated automatically, without the intervention of an auxiliary hydraulic circuit or of any associated mechanical means or of an electric or electronic circuit. This results in simplicity, economy and reliability, both in the construction and in the operation of the artificial kidney.

A side tube (23), which is provided with flow-adjusting means, for example an adjusting valve (24), is connected to the loop circuit (15) at a point which is located between the chamber (19) and the reservoir (16) and preferably located just below the level of liquid in the chamber (19).

A graduated receiver (25) makes it possible to measure, at any time, the volume of liquid collected from the side tube (23), which generally does not exceed a few liters.

The operation of the artificial kidney shown in FIG. 1 is as follows. The dialysis liquid is introduced beforehand into the circuit (15), which is filled, for example, with the aid of the tube (23) and the pump (17). An essentially constant level can be established in the chamber (19) when, with the float (21) raised by the dialysis liquid, the point (22) engages inside the flared orifice (20), thus limiting the passage area for the dialysis liquid.

The blood is then caused to circulate in the hemodialyzer, in which, mainly under the effect of the pump (14) and the pressure losses downstream of the pump, in particular of the fistula for reinjecting the blood into the patient, the blood exerts, on the membrane, an average pressure which is constantly greater than atmospheric pressure, and this pressure can easily be kept at values which are greater than, or at least equal to, the pressure of the dialysis liquid in the hemodialyzer, taking into account the osmotic pressure of the blood, which is referred to as the oncotic pressure.

With the circuit (15) filled, the valve (24) is closed and it is supposed, for example, that the point (22) allows the dialysis liquid to flow freely through the orifice (20) into the chamber (19). With atmospheric pressure being exerted on the surface of the dialysis liquid in the chamber (19), the average pressure of the dialysis liquid in the hemodialyzer is established at a minimum value which is greater than atmospheric pressure and which can be kept below that of the blood. As a result, there is an average pressure difference, the trans-membrane pressure, between the compartments (12) and (13) of the hemodialyzer, the effect of this pressure difference being to create, across the membrane, a flow of ultrafiltrate running from the blood towards the dialysis liquid.

This flow increases the volume of liquid present in the essentially invariable circuit (15). It raises the level of the liquid in the chamber (19) and hence the level of the float (21), and this leads to the progressive closing of the obturator (20,22) until, with the pressure of the dialysis liquid increasing uniformly, this pressure reaches a value for which the flow of ultrafiltrate becomes zero.

The float then remains at a constant level and an equilibrium is established. If the blood pressure undergoes various fluctuations during the treatment, the blocking device regulates automatically the pressure of the dialysis liquid at any time, in order to keep the flow of ultrafiltrate constantly at a zero value.

Suppose that it is now decided to remove a fixed amount of ultrafiltrate from the patient; it suffices to open the valve (24) and then to draw off and measure, in the graduated receiver (25), an amount of liquid equal to the amount of ultrafiltrate which it is desired to remove.

In fact, either a fixed volume or a fixed flow rate of ultrafiltrate will be removed, as desired, by fixing the extent and the duration of opening of the valve (24). These conditions of opening of the valve (24) can permit either an immediate removal, or a removal at a constant flow rate, or also a removal at a variable flow rate, in accordance with an appropriate program chosen by the person responsible for the treatment, as a function of the state and the behaviour of the patient, with the aid of any device which is in itself known for controlling the opening of the valve as a function of this program.

As soon as the valve (24) opens, the float descends, freeing the obturator, and this causes the pressure of the dialysis liquid to drop, in particular in the hemodialyzer. Under the effect of the trans-membrane pressure thus obtained, the blood ultrafilters across the membrane. The amount of ultrafiltrate collected in the circuit (15) causes the level of the dialysis liquid in the chamber (19), and hence the float, to rise progressively, and this tends progressively to close the obturator again. This movement continues until the amount of ultrafiltrate exactly compensates the amount of liquid drawn off from the circuit (15) and collected in the graduated receiver (25).

The device described thus has the effect of instantaneously regulating, directly or automatically, the transmembrane pressure and hence the amount (volume or flow rate) of ultrafiltrate across the membrane, in order to keep it constantly equal to the amount (volume or flow rate) of liquid intentionally removed from the dialysis liquid circuit (15).

This artificial kidney exhibits the advantage of permitting operation, as has been seen, with a zero ultrafiltration rate. It also possesses its own safety features. Thus, if for any reason, for example an incorrect manuever during filling, the level of the dialysis liquid in the circuit (15) rises above a normal value, all or part of the excess can flow through the tube (18) which, if necessary, functions as a syphon. On the one hand, the excess liquid can be collected in the receiver (25); it can thus be measured and it can be taken into account in the assessment of the treatment. On the other hand, there is thus no risk of any dangerous pressure being exerted on the membrane or on the blood.

Conversely, if some liquid flows out abruptly through the tube (23), only the volume of liquid above the level of the tube (23) would escape by gravity, and it is easy to limit this volume or this flow rate automatically, both in the construction and during the use of the artificial kidney.

Moreover, this system is particularly economical. The volume of the chamber (19) is not critical and it is shown in the figure, on a different scale from the other elements of the circuit, only for greater clarity. In fact, the various elements of the loop circuit can advantageously be designed to be used once only, in order to avoid any prior sterilization treatment. For this purpose, it is preferred to line the invariable reservoir (16) with a flexible, impermeable, detachable plastics bag, which is connected to the inlet and/or outlet orifices of this reservoir. Thus, after each session, only the bag is thrown away and the reservoir itself can be re-used without having to be sterilized.

Figure 2:
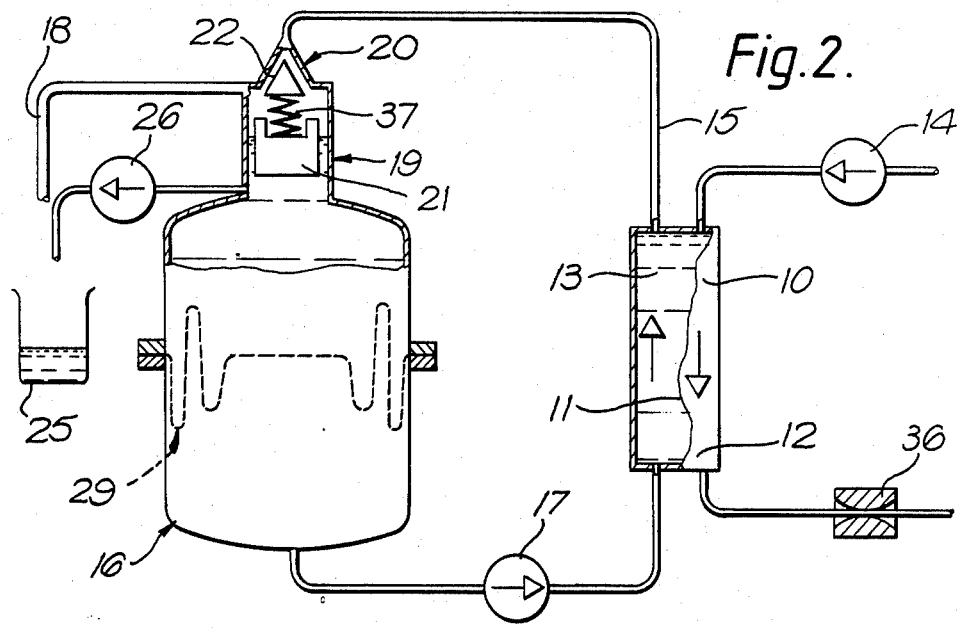
FIG. 2 is the diagram of a second embodiment of an artificial kidney according to the invention.
Figure 3:
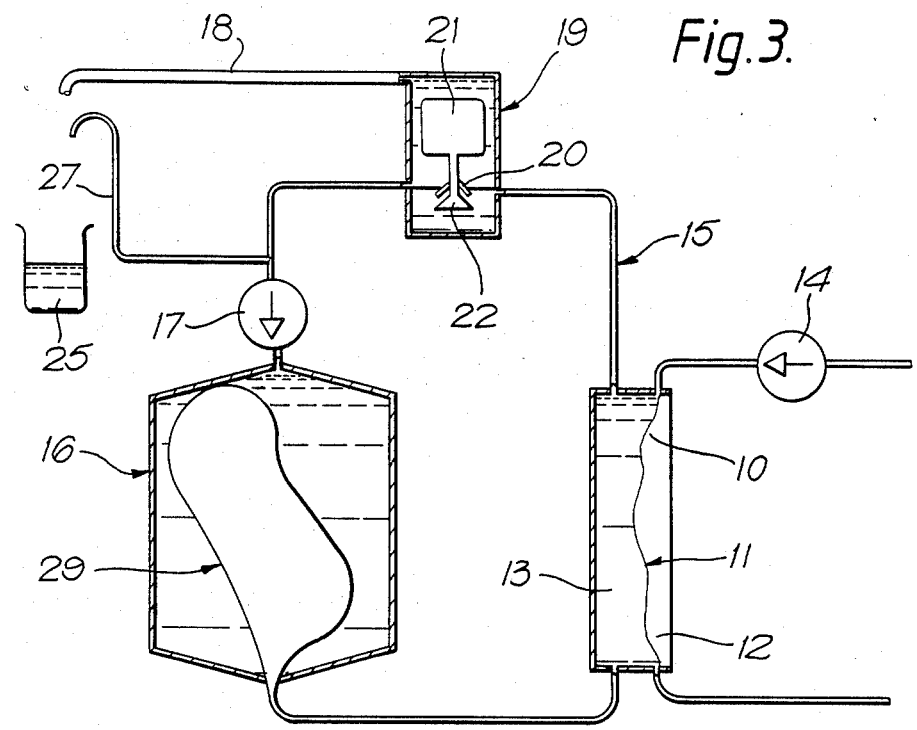
FIG. 3 is the diagram of a third embodiment of an artificial kidney according to the invention.
Figure 4:
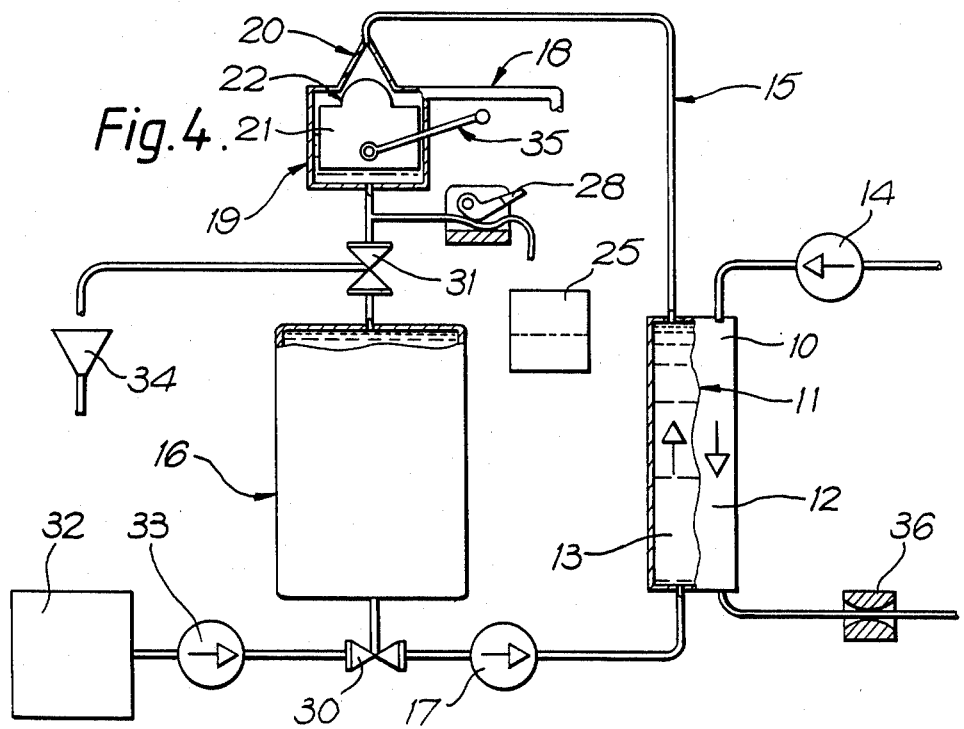
FIG. 4 is the diagram of a fourth embodiment of an artificial kidney according to the invention.

Various alternative embodiments of the invention can be used. By way of examples, FIGS. 2, 3 and 4 show some of these embodiments. Of course, various combinations may be used of the various particular arrangements shown in different ones of the figures without departing from the scope of the invention.

The regulating device with a float-type obturator can consist of any known means. Thus, by way of example, the chamber (19) shown in FIG. 2 is incorporated into the reservoir (16), and the float (21) can have various shapes, which may or may not be bodies of revolution, can be open in the lower bell-shaped part (FIG. 1) or can constitute a hollow or solid, closed volume (FIGS. 2, 3 and 4), in which case it can consist of an expanded material. The float can be guided by any known means, for example by the inner walls of the chamber (19) or by an articulated lever (35) (FIG. 4). The point is preferably conical, but it can have any other suitable shape, for example a hemispherical shape (FIG. 4).

The blocking point can be incorporated into the float (FIGS. 1 and 4). It can be joined rigidly to the float (FIG. 3) and thus be integral with the float. It can also be joined elastically to the float (FIG. 2), for example via a spring, which can have a step-down action between the level of the dialysis liquid in the chamber (19) and the pressure of the dialysis liquid, in particular in the hemodialyzer. The blocking device can be located either above the float (FIGS. 1, 2 and 4) or below (FIG. 3). It is possible to use one or more floats and/or blocking devices. For example, two distinct float/obturator units (not shown) of different dimensions, with a staggered blocking action, can be arranged in parallel, the finest regulation thus being provided only by the smaller unit.

The means for drawing off liquid from the dialysis liquid loop circuit can consist either of an adjusting valve (24) (FIG. 1) or of an adjustable clamp (28) (FIG. 4) or of a simple adjustable-height overflow (27) (FIG. 3) or, preferably an occlusive pump (26) (FIG. 2), which can impose the removal of predetermined amounts of liquid, regardless, in particular, of the degree of clogging of the membrane. A volumeter of any known type (not shown), which measures, integrates and/or records, with precision, the volume of liquid delivered, can be associated with this pump. It is noted that the pump (26) can be used to remove dialysis liquid at any rate, without the slightest risk, even at a rate greater than the flow rate of the ultrafiltrate across the membrane (11).

The pump (17) for circulating dialysis liquid is advantageously arranged upstream of the hemodialyzer (10), preferably between the reservoir (16) and the hemodialyzer (10). It can also (compare FIG. 3) be arranged between the chamber (19) and the reservoir (16), pushing the used dialysis liquid into the reservoir (16) and thus displacing, with the same pressure across a flexible diaphragm (29), the same amount of fresh dialysis liquid throught the hemodialyzer (10).

The reservoir (16) is invariable; it is preferably cylindrical and provided with conical (FIG. 3) or semi-elliptical (FIGS. 1 and 2) ends. With the embodiment of FIG. 1, the dialysis liquid can be recycled into the hemodialyzer up to the end of the treatment. If necessary, the dialysis liquid can pass through a purifying filter, for example packed with active charcoal, which is not shown.

However, it is preferred to carry out the operation in a single pass, that is to say to pass the dialysis liquid through the hemodialyzer only once. A flexible diaphragm (29) (FIGS. 2 and 3) provides a leaktight separation between the fresh dialysis liquid and the used liquid.

It is also possible to use a reservoir (16) of very reduced volume if, as shown in FIG. 4, the reservoir (16) is simultaneously and periodically connected, by means of two three-way valves (30) and (31), on the one hand to a supply (32) of fresh dialysis liquid with the aid of a pump (33), and on the other hand to the waste outlet (34). A flexible and leaktight diaphragm (not shown) can, if necessary, constantly keep the fresh dialysis liquid separated from the used dialysis liquid.

The operation of the installation shown in FIG. 4 is thus as follows. The three-way taps enable the dialysis liquid to circulate normally in the loop circuit (15) by virtue of the pump (17), until the used liquid has to be replaced by fresh liquid. Periodically, therefore, the three-way valves (30) and (31) simultaneously isolate the rest of the dialysis liquid loop circuit and make it possible to replace the used dialysis liquid by an equal volume of fresh dialysis liquid, which is subjected to a new cycle. If desired, a by-pass (not shown) can connect the chamber (19) to the suction orifice of the pump (17) so as not to interrupt the circulation of the dialysis liquid during the replacement of the used dialysis liquid in the reservoir (16).

If necessary, a device for partially closing the blood circuit, such as a clamp (36) (FIGS. 2 and 4), can be arranged downstream of the hemodialyzer so as to increase the blood pressure in the hemodialyzer, if necessary, in order to prevent it from being below the pressure of the dialysis liquid. Thus, there is always the possibility of maintaining a positive or zero transmembrane pressure, making it possible to treat the blood by simultaneous dialysis and ultrafiltration. If appropriate, the closing of the clamp can be governed or controlled by a device which is in itself known for comparing the amount of liquid collected in the receiver (25) with the amount of ultrafiltrate which it is desired to withdraw.

If the membrane (11) is of the fast-flow type, that is to say of the type having a permeability to water which is greater than or equal to 15 ml/hour$\times$m$^2\times$mm Hg, a sufficient ultrafiltration rate is obtained for a relatively low trans-membrane pressur and, under these conditions, the use of the clamp (36) is generally not necessary.

Of course, it is also possible to combine an artificial kidney embodying the invention with a device, of any type which is in itself known, for treating the blood by plasmapheresis.

I claim:

1. In a hemodialysis apparatus for treating blood of a patient by dialysis and by withdrawing from blood appropriate amounts of ultrafiltrate through a semipermeable membrane dividing a hemodialyzer into two compartments respectively for blood and dialysis liquid, the hemodialysis apparatus comprising a circuit for the dialysis liquid including the hemodialyzer and one circulating pump, the circuit being formed as a loop of constant volume, being open to the atmosphere and provided with means for drawing off predetermined amounts of dialysis liquid from the circuit corresponding to equal amounts of ultrafiltrate to be withdrawn from the blood of a patient and means for measuring the amount of dialysis liquid drawn off, a float supported by dialysis liquid in said circuit, and provided in the circuit downstream of the hemodialyzer with an automatic variable hydraulic resistance means consisting of an obturator operable to resist flow through said circuit and having a movable part joined to said float for controlling operation of said obturator, the obturator maintaining an essentially constant level of dialysis liquid in the circuit and regulating positive pressure of the dialysis liquid in the hemodialyzer as a function of the amounts of ultrafiltrate withdrawn from the blood.

2. The hemodialysis apparatus according to claim 1, wherein the moving part of the obturator is joined rigidly to the float.

3. The hemodialysis apparatus according to claim 1, wherein the moving part of the obturator is joined elastically to the float.

4. The hemodialysis apparatus according to claim 1, including in the circuit a leaktight and flexible diaphragm which separates used dialysis liquid from fresh dialysis liquid.

5. The hemodialysis apparatus according to claim 1, including a source of fresh dialysis liquid, a waste outlet and means for periodically replacing used dialysis liquid in said circuit by fresh dialysis liquid, the said means being operable simultaneously to connect a reservoir to a said source of fresh dialysis liquid and to the waste outlet.

6. The hemodialysis apparatus according to claim 1, wherein said float is movable under a fixed orifice and may be pushed up and down according to the level of the dialysis liquid in order to respectively block and free said orifice, thus ensuring the automatic regulation of the pressure of the dialysis liquid in said hemodialyzer.

* * * * *